US009562005B2

(12) United States Patent
Bury et al.

(10) Patent No.: US 9,562,005 B2
(45) Date of Patent: Feb. 7, 2017

(54) METALLATED METAL-ORGANIC FRAMEWORKS

(71) Applicant: Northwestern University, Evanston, IL (US)

(72) Inventors: Wojciech Bury, Evanston, IL (US); Omar K. Farha, Glenview, IL (US); Joseph T. Hupp, Northfield, IL (US); Joseph E. Mondloch, Park Ridge, IL (US)

(73) Assignee: Northwestern University, Evanston, IL (US)

( * ) Notice: Subject to any disclaimer, the term of this patent is extended or adjusted under 35 U.S.C. 154(b) by 52 days.

(21) Appl. No.: 14/333,792

(22) Filed: Jul. 17, 2014

(65) Prior Publication Data

US 2015/0031908 A1 Jan. 29, 2015

Related U.S. Application Data

(60) Provisional application No. 61/857,314, filed on Jul. 23, 2013.

(51) Int. Cl.

*A62D 3/33* (2007.01)
*C07C 253/30* (2006.01)
*B01J 20/22* (2006.01)
*B01J 20/32* (2006.01)
*C23C 16/04* (2006.01)
*C23C 16/18* (2006.01)
*C23C 16/455* (2006.01)
*B01J 31/16* (2006.01)
*B01J 31/22* (2006.01)
*C02F 1/28* (2006.01)
*C02F 101/20* (2006.01)

(52) U.S. Cl.

CPC ............ *C07C 253/30* (2013.01); *B01J 20/226* (2013.01); *B01J 20/3236* (2013.01); *B01J 31/1691* (2013.01); *B01J 31/2239* (2013.01); *C02F 1/285* (2013.01); *C23C 16/045* (2013.01); *C23C 16/18* (2013.01); *C23C 16/45555* (2013.01); *B01J 2231/342* (2013.01); *B01J 2531/48* (2013.01); *C02F 1/281* (2013.01); *C02F 1/288* (2013.01); *C02F 2101/20* (2013.01)

(58) Field of Classification Search

CPC .............. A62D 3/33; B01J 21/04; B01J 21/02
USPC .................. 588/315, 407, 412, 901; 502/439
See application file for complete search history.

(56) References Cited

U.S. PATENT DOCUMENTS 8,715,395 B2 5/2014 Omary
8,962,875 B2 * 2/2015 Norman .................. C07F 17/00 427/252
2006/0252641 A1 11/2006 Yaghi et al.
2011/0046335 A1 2/2011 Fernandes
2011/0297558 A1 12/2011 Hill
2012/0201860 A1 * 8/2012 Weimer ............. B01D 67/0002 424/400
2012/0297982 A1 11/2012 Dinca et al.
2013/0139686 A1 6/2013 Wilmer
2013/0296162 A1 11/2013 Wright
2015/0031908 A1 1/2015 Bury
2015/0217268 A1 8/2015 Farha et al.

FOREIGN PATENT DOCUMENTS

EP 2578593 4/2013

OTHER PUBLICATIONS

Burnett et al., Stepwise Synthesis of Metal-Organic Frameworks: Replacement of Structural Organic Linkers, J. Am. Chem. Soc., vol. 133, Jun. 15, 2011, pp. 9984-9987.
Bury et al., Control over Catenation in Pillared Paddlewheel Metal-Organic Framework Materials via Solvent-Assisted Linker Exchange, Chem. Mater., vol. 25, Feb. 9, 2013, pp. 739-744.
Dalvi et al., Understanding the Effectiveness of Fluorocarbon Ligands in Dispersing Nanoparticles in Supercritical Carbon Dioxide, J. Phys. Chem. C, vol. 114, Aug. 31, 2010, pp. 15553-15561.
Deria et al., Perfluoroalkane Functionalization of NU-1000 via Solvent-Assisted Ligand Incorporation: Synthesis and CO2 Adsorption Studies, J. Am. Chem. Soc., vol. 135, Oct. 31, 2013, pp. 16801-16804.
DeSimone et al., Dispersion Polymerizations in Supercritical Carbon Dioxide, Science, vol. 265, Jul. 15, 1994, pp. 356-359.
Farha et al., An Example of Node-Based Postassembly Elaboration of a Hydrogen-Sorbing, Metal-Organic Framework Material, Inorg. Chem., vol. 47, Oct. 18, 2008, pp. 10223-10225.
Fernandez et al., Gas-Induced Expansion and Contraction of a Fluorinated Metal-Organic Framework, Crystal Growth & Design, vol. 10, No. 3, Jan. 29, 2010, pp. 1037-1039.
Fried et al., the molecular basis of CO2 interaction with polymers containing fluorinated groups: computational chemistry of model compounds and molecular simulation of poly[bis(2,2,2-trifluoroethoxy)phosphazene], Polymer, vol. 44, 2003, pp. 4363-4372.
Hwang et al., Amine Grafting on Coordinatively Unsaturated Metal Centers of MOFs: Consequences for Catalysis and Metal Encapsulation, Angew. Chem. Int. Ed., vol. 47, Apr. 24, 2008, pp. 4144-4148.
Seo et al., A homochiralmetal-organic porous material for enantioselective separation and catalysis, Nature, vol. 404, Apr. 27, 2000, pp. 982-986.
Kanoo et al., Unusual room temperature CO2 uptake in a fluoro-functionalized MOF: insight from Raman spectroscopy and theoretical studies, Chem. Commun., vol. 48, Jun. 29, 2012, pp. 8487-8489.

(Continued)

*Primary Examiner* — Edward Johnson
(74) *Attorney, Agent, or Firm* — Bell & Manning, LLC

(57) ABSTRACT

Porous metal-organic frameworks (MOFs) and metallated porous MOFs are provided. Also provided are methods of metallating porous MOFs using atomic layer deposition and methods of using the metallated MOFs as catalysts and in remediation applications.

14 Claims, 8 Drawing Sheets

(56) References Cited

OTHER PUBLICATIONS

Karagiaridi et al., Opening Zif-8: A Catalytically Active Zeolitic Imidazolate Framework of Sodalite Topology with Unsubstituted Linkers, J. Am. Chem. Soc., vol. 134, Oct. 22, 2012, pp. 18790-18796.
Karagiaridi et al., Synthesis and characterization of isostructural cadmium zeolitic imidazolate frameworks via solvent-assisted linker exchange, Chem. Sci., vol. 3, Aug. 7, 2012, pp. 3256-3260.
Kiang et al., Variable Pore Size, Variable Chemical Functionality, and an Example of Reactivity within Porous Phenylacetylene Silver Salts, J. Am. Chem. Soc., vol. 121, Aug. 25, 1999, pp. 8204-8215.
Kim et al., Postsynthetic ligand exchange as a route to functionalization of 'inert' metal-organic frameworks, Chem. Sci., vol. 3, Sep. 13, 2011, pp. 126-130.
Li et al., Stepwise Ligand Exchange for the Preparation of a Family of Mesoporous MOFs, J. Am. Chem. Soc., vol. 135, May 20, 2013, pp. 11688-11691.
Mondloch et al., Vapor-Phase Metalation by Atomic Layer Deposition in a Metal-Organic Framework, J. Am. Chem. Soc., vol. 135, Jul. 5, 2013, pp. 10294-10297.
Noro et al., Highly Selective CO2 Adsorption Accompanied with Low-Energy Regeneration in a Two-Dimensional Cu(II) Porous Coordination Polymer with Inorganic Fluorinated PF6- Anions, Inorg. Chem., vol. 52, Dec. 18, 2012, pp. 280-285.
Nugent et al., Porous materials with optimal adsorption thermodynamics and kinetics for CO2 separation, Nature, vol. 495, Feb. 27, 2013, pp. 80-84.
Takaishi et al., Solvent-assisted linker exchange (SALE) and post-assembly metallation in porphyrinic metal-organic framework materials, Chem. Sci., vol. 4, Dec. 7, 2012, pp. 1509-1513.
Wilmer et al., Structure-property relationships of porous materials for carbon dioxide separation and capture, Energy Environ. Sci., vol. 5, Sep. 21, 2012, pp. 9849-9856.
Xue et al., Tunable Rare-Earth fcu-MOFs: A Platform for Systematic Enhancement of CO2 Adsorption Energetics and Uptake, J. Am. Chem. Soc., vol. 135, Apr. 22, 2013, pp. 7660-7667.
Yang et al., Fluorous Metal-Organic Frameworks with Superior Adsorption and Hydrophobic Properties toward Oil Spill Cleanup and Hydrocarbon Storage, J. Am. Chem. Soc., vol. 133, Oct. 7, 2011, pp. 18094-18097.
Yaghi et al., Reticular synthesis and the design of new materials, Nature, vol. 423, Jun. 12, 2003, pp. 705-714.
G. Férey, Hybrid porous solids: past, present, future, Chemical Society Reviews, vol. 37, Sep. 19, 2007, pp. 191-214.
Horike et al., Soft porous crystals, Nature Chemistry, vol. 1, Nov. 23, 2009, pp. 695-704.
Lee et al., Metal-organic framework materials as catalysts, Chemical Society Reviews, vol. 38, Mar. 17, 2009, pp. 1450-1459.
Dinca et al., Hydrogen Storage in Microporous Metal-Organic Frameworks with Exposed Metal Sites, Angewandte Chemie Int. Ed., vol. 47, Aug. 8, 2008, pp. 6766-6779.
Bae et al., High Propene/Propane Selectivity in Isostructural Metal-Organic Frameworks with High Densities of Open Metal Sites, Angewandte Chemie Int. Ed., vol. 51, Jan. 16, 2012, pp. 1857-1860.
S. Cohen, Postsynthetic Methods for the Functionalization of Metal-Organic Frameworks, Chemical Reviews, vol. 112, Sep. 14, 2011, pp. 970-1000.
Sumida et al., Impact of Metal and Anion Substitutions on the Hydrogen Storage Properties of M-BTT Metal-Organic Frameworks, Journal of the American Chemical Society, vol. 135, Dec. 17, 2012, pp. 1083-1091.
Meilikhov et al., Metals@MOFs-Loading MOFs with Metal Nanoparticles for Hybrid Functions, European Journal of Inorganic Chemistry, vol. 2010, No. 24, Jul. 9, 2010, pp. 3701-3714.
S. George, Atomic Layer Deposition: An Overview, Chemical Reviews, vol. 110, No. 1, Nov. 30, 2009, pp. 111-131.
R. Puurunen, Surface chemistry of atomic layer deposition: A case study for the trimethylaluminum/water process, Journal of Applied Physics, vol. 97, No. 121301, Jun. 30, 2005, pp. 1-52.
Marichy et al., Atomic Layer Deposition of Nanostructured Materials for Energy and Environmental Applications, Advanced Materials, vol. 24, Jan. 26, 2012, pp. 1017-1032.
J. Elam, Chapter 10, Coatings on High Aspect Ratio Structures, Atomic Layer Deposition of Nanostructured Materials, First Edition, Edited by Nicola Pinna and Mato Knez, Published 2012 by Wiley-VCH Verlag GmbH & Co. KGaA, Jan. 2, 2012, pp. 227-249.
Lu et al., Coking- and Sintering-Resistant Palladium Catalysts Achieved Through Atomic Layer Deposition, Science, vol. 335, Mar. 9, 2012, pp. 1205-1208.
Liu et al., Robust, Functional Nanocrystal Solids by Infilling with Atomic Layer Deposition, Nano Letters, vol. 11, Oct. 24, 2011, pp. 5349-5355.
Hamann et al., Aerogel Templated ZnO Dye-Sensitized Solar Cells, Advanced Materials, vol. 20, Apr. 9, 2008, pp. 1560-1564.
Cavka et al., A New Zirconium Inorganic Building Brick Forming Metal Organic Frameworks with Exceptional Stability, Journal of the American Chemical Society, vol. 130, Sep. 26, 2008, pp. 13850-13851.
Morris et al., Synthesis, Structure, and Metalation of Two New Highly Porous Zirconium Metal-Organic Frameworks, Inorganic Chemistry, vol. 51, Jun. 7, 2012, pp. 6443-6445.
Feng et al., Zirconium-Metalloporphyrin PCN-222: Mesoporous Metal-Organic Frameworks with Ultrahigh Stability as Biomimetic Catalysts, Angewandte Chemie Int. Ed., vol. 51, Aug. 21, 2012, pp. 10307-10310.
Bon et al., Zr- and Hf-Based Metal-Organic Frameworks: Tracking Down the Polymorphism, Crystal Growth & Design, vol. 13, No. 3, Feb. 14, 2013, pp. 1231-1237.
Gordon et al., A Kinetic Model for Step Coverage by Atomic Layer Deposition in Narrow Holes or Trenches , Chemical Vapor Deposition, vol. 9, No. 2, 2003, pp. 73-78.
Elam et al., Conformal Coating on Ultrahigh-Aspect-Ratio Nanopores of Anodic Alumina by Atomic Layer Deposition, Chemistry of Materials, vol. 15, No. 18, Aug. 14, 2003, pp. 3507-3517.
Valenzano et al., Disclosing the Complex Structure of UiO-66 Metal Organic Framework: A Synergic Combination of Experiment and Theory, Chemistry of Materials, vol. 23, Mar. 4, 2011, pp. 1700-1718.
Larabi et al., Titration of $Zr_3$(μ-OH) Hydroxy Groups at the Cornerstones of Bulk MOF UiO-67, [$Zr_6O_4(OH)_4$(biphenyldicarboxylate)$_6$], and Their Reaction with [AuMe($PMe_3$)], European Journal of Inorganic Chemistry, vol. 2012, No. 18, May 11, 2012, pp. 3014-3022.
He et al., Infrared Studies of the Adsorption of Synthesis Gas on Zirconium Dioxide , Journal of Catalysis, vol. 87, 1984, pp. 381-388.
Cui et al., Stereoselective construction of fluorinated indanone derivatives via a triple cascade Lewis acid-catalyzed reaction, Chemical Communications, vol. 2007, No. 22, Apr. 4, 2007, pp. 2284-2286.
Deria, P., et al., "Versatile functionalization of the NU-1000 platform by solvent-assisted ligand incorporation," *Chemical Communications*, Jan. 9, 2014, vol. 50, No. 16, 4 pp.
International Search Report and Written Opinion for Intl. Patent Appl. No. PCT/2015/014082, mailed on May 29, 2015, 11 pp.
International Search Report and Written Opinion mailed in PCT/US15/61475, Mar. 4, 2016.
Beyzavi et al., A hafnium-based metal organic framework as an efficient and multifunctional catalyst for facile CO2 fixation and regioselective and enantioretentive epoxide activation, Journal of the American Chemical Society, vol. 136, No. 45, Oct. 30, 2014, pp. 15861-15864.
Stephenson et al., Research update: A hafnium-based metalorganic framework as a catalyst for regioselective ring-opening of epoxides with a mild hydride source, APL Materials, vol. 2, No. 12, article No. 123901, Oct. 27, 2014, pp. 1-5.

(56) References Cited

OTHER PUBLICATIONS

Furukawa et al., The chemistry and applications of metal-organic frameworks, Science, vol. 341, article No. 1230444, Aug. 30, 2013.

* cited by examiner

METALLATED METAL-ORGANIC FRAMEWORKS

CROSS-REFERENCE TO RELATED APPLICATIONS

The present application claims priority to U.S. Provisional Patent Application No. 61/857,314 that was filed Jul. 23, 2013, the entire contents of which is hereby incorporated by reference.

REFERENCE TO GOVERNMENT RIGHTS

This invention was made with government support under contract number DE-AC05-06OR23100 (Subcontract No. 10-20903 DOE, Oak Ridge, Tenn.) awarded by the Department of Energy. The government has certain rights in the invention.

BACKGROUND

Metal-organic frameworks (MOFs) are a class of hybrid materials comprising inorganic nodes and organic linkers. In many instances coordinatively unsaturated metal sites—either at the linkers or the nodes—are essential for engendering desired functional behavior. These sites can facilitate catalysis, gas storage, and gas separation.

MOFs have been metal-functionalized from the condensed phase (i.e., solution) either in de novo fashion or via post-synthesis modification. (See, Gordon, R. G.; Hausmann, D.; Kim, E.; Shepard, J. *Chem. Vapor Depos*. 2003, 9, 73.) Unfortunately, considerable effort (in the form of purification and activation) is necessary to ensure that excess metals, and/or undesired solvent and other reagents, are removed from solution-metallated MOFs. Solvent molecules can also irreversibly ligate otherwise coordinatively unsaturated metal sites, yielding, in turn, less-than-desirable materials properties.

Meilikhov et al. demonstrated that a variety of metal inclusion compounds (i.e., "metal@MOF" host-guest complexes) could be synthesized utilizing chemical vapor infiltration from volatile metal complexes under "sublimation-like" conditions. (See, Meilikhov, M.; Yusenko, K.; Esken, D.; Turner, S.; Van Tendeloo, G.; Fischer, R. A. *Eur. J. Inorg. Chem*. 2010, 3701.) However, little control can be obtained over the spatial distribution of the metal species within the MOF and, in some instances, the resulting metal@MOF structures are unstable.

SUMMARY

Porous metal-organic frameworks, metallated porous metal-organic frameworks and methods of making and using them are provided.

The methods of metallating a porous metal-organic framework comprise depositing a film comprising a metal on the surfaces within the pores of the metal-organic framework via atomic layer deposition. An example of a porous metal-organic framework suitable for metallation has the formula $Zr_6(\mu_3\text{-}OH)_8(OH_8)(TBAPy)_2$.

In some embodiments of the metallated metal-organic frameworks the metal film comprises catalytic sites. Such embodiments can be used to catalyze a reaction by exposing chemical reactants to the metallated metal-organic framework under conditions in which the metal film catalyzes the reaction.

In some embodiment of the metallated metal-organic frameworks the metal film comprises sorption sites. Such embodiments can be used in remediation applications by exposing a sample to the metallated metal-organic framework, whereby species in the sample are adsorbed or absorbed at the sorption sites of the metallated metal-organic framework, and removing the metallated metal-organic framework and adsorbed or absorbed species from the sample.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings.

DETAILED DESCRIPTION

Porous MOFs and metallated porous MOFs are provided. Also provided are methods of metallating the porous MOFs using atomic layer deposition and methods of using the metallated MOFs as catalysts and in remediation applications.

The MOFs have a structure comprising inorganic (e.g., metal) nodes, also referred to as centers, coordinated via organic molecular linkers to form a highly connected porous network. The surfaces of the interior pores of the MOF can be metallated using atomic layer deposition (ALD). ALD is a vapor-phase synthetic technique for depositing thin-films. Unlike other vapor-phase deposition techniques (e.g., chemical vapor deposition/infiltration) the precursor molecules in ALD deposit only at chemically reactive surface sites and do not react with themselves—that is, the reactions are self-limiting. As a result, ALD can be used in a layer-by-layer film deposition process using cycle exposures of precursor molecules with intervening purge cycles. The process for metallating a MOF via ALD is referred to herein as AIM (metallation by ALD in a MOF).

The MOFs used in the AIM process are desirably characterized by the following properties: (1) they have mesoporous channels in order to facilitate the diffusion of ALD reactants within the MOF; (2) they are thermally and hydrolytically stable at temperatures in the range from 100-300° C.; and (3) the surfaces of their pores are functionalized with spatially oriented functional groups that are able to react with ALD precursors to facilitate self-limiting film-forming reactions via ALD. As used herein, the term mesoporous refers to porous materials having an average pore size in the range from about 2 to about 50 nm. Methods of measuring pore sizes are described in the example. Hydroxyl groups (—OH) are an example of a functional group that reacts with ALD precursor molecules. Other examples of suitable functional groups include water ($H_2O$), carboxylic acids (R—COOH), amine groups having a lone pair of electrons or a basic proton (e.g., ethylenediamine or triethylenediamine), and base groups comprising one or more O, S, P or C atoms, such as those from sulfonic acid (R—$SO_3H$) and phosphonic acid (e.g., R—$PO_3H$).

Figure 2:
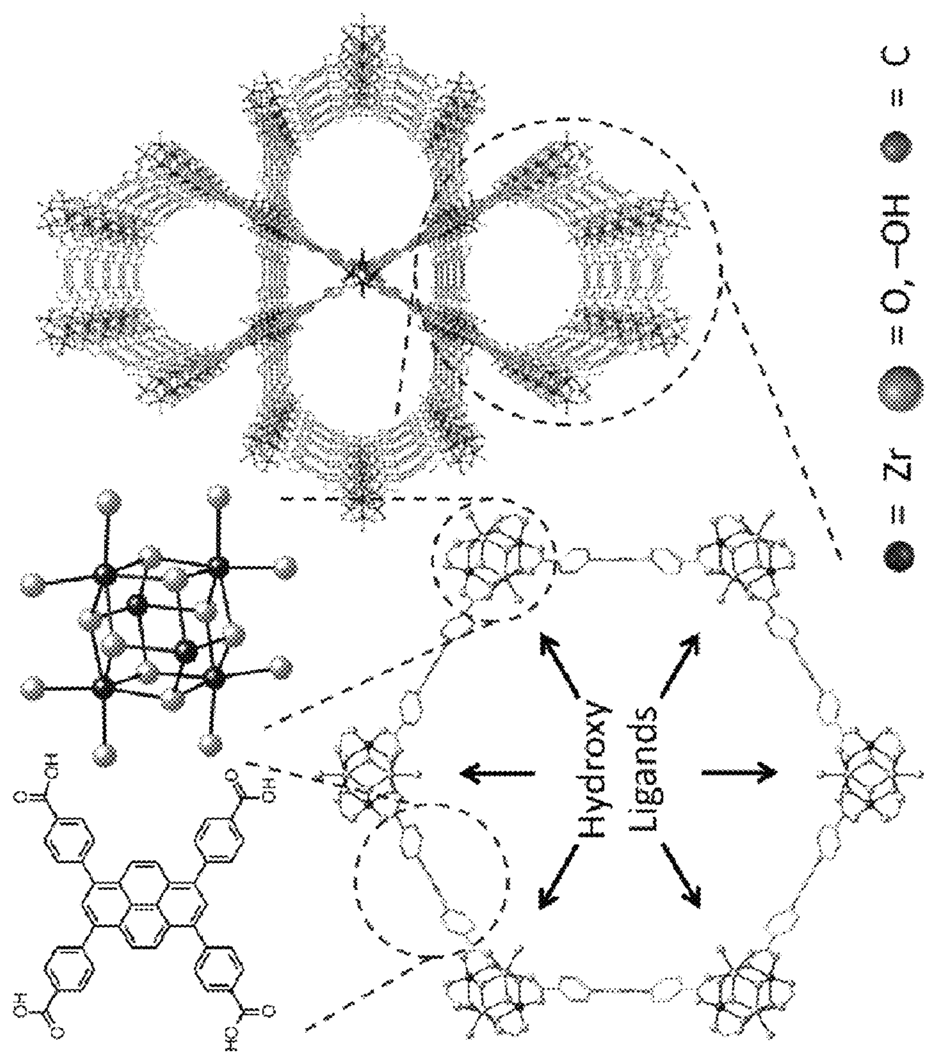
FIG. 2. Relevant structural features and representations of NU-1000. For simplicity hydrogen atoms are not shown.

Examples of MOFs having all of the above-referenced properties are zirconium MOFs constructed from hexa-$Zr^{IV}$ nodes and tetratopic linkers. Such MOFs are stable to 500° C., can contain mesoporous channels and can contain spatially oriented —OH groups. (See, Cavka, J. H.; Jakobsen, S.; Olsbye, U.; Guillou, N.; Lamberti, C.; Bordiga, S.; Lillerud, K. P. *J. Am. Chem. Soc.* 2008, 130, 13850; Morris, W.; Volosskiy, B.; Demir, S.; Gándara, F.; McGrier, P. L.; Furukawa, H.; Cascio, D.; Stoddart, F. J.; Yaghi, O. M. *Inorg. Chem.* 2012, 51, 6443.) A specific example of a zirconium MOF that can be metallated using the AIM process has the molecular formula $Zr_6(\mu_3\text{-}OH)_8(OH)_8(TBAPy)_2$ and the structure shown in FIG. 2. This MOF is referred to herein as NU-1000. Alternative formulations of the structure of NU-1000 comprise oxo and aquo ligands in place of hydroxo ligands. Both of these alternative formulations are capable of undergoing AIM to provide a metallated MOF.

Figure 8:
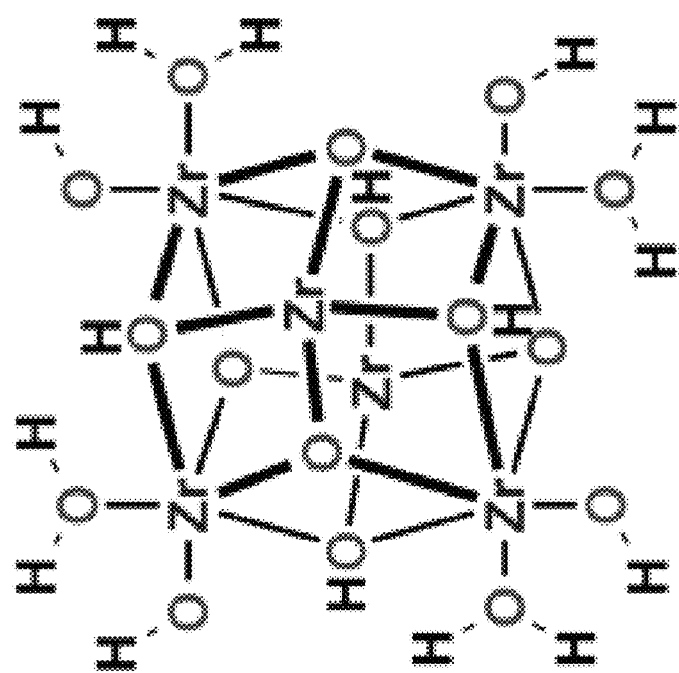
FIG. 8. A $Zr_6$-based node of NU-1000 comprising a staggered mixed proton topology with the molecular formula $[Zr_6(\mu_3\text{-}O)_4(\mu_3\text{-}OH)_4(OH)_4(H_2O)_4]^{8+}$.

Thus, for embodiments of the MOFs comprising aquo ligands, the molecular formula for the MOF can be described more generally as having nodes represented by the formula $[Zr_6(\mu_3\text{-}O)_8(O)_8(H_{16})]^{8+}$ bridged by tetracarboxylate linkers. An example of a node comprising aquo ligands in place of some hydroxo ligands is depicted in FIG. 8. This isomer of the node, comprises a staggered mixed proton topology with the formula $[Zr_6(\mu_3\text{-}O)_4(\mu_3\text{-}OH)_4(OH)_4(H_2O)_4]^{8+}$.

Figure 1:
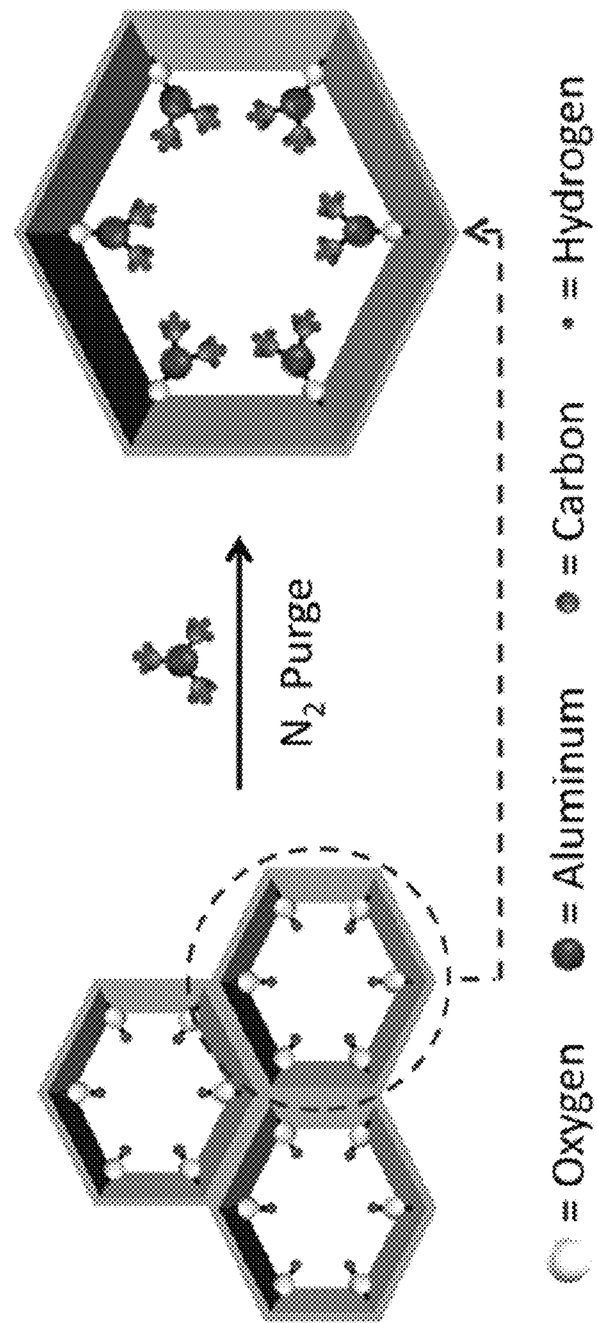
FIG. 1. An illustration of metallation by ALD in a MOF (AIM).

A schematic diagram illustrating the AIM process is shown in FIG. 1, where the MOF structure is represented by a matrix of hexagonal pores. In this embodiment, the interior surfaces of the pores are functionalized by hydroxyl groups that react with a metal-containing ALD precursor molecule, such as a metal-organic molecule, to provide a film comprising the metal on the surface of the pores. The ALD process illustrated in this figure uses cyclic exposures of trimethylaluminum, as the metal-containing precursor molecule, with a nitrogen purge cycle.

The films deposited within the pores of the MOF include films comprising a single metal element and films comprising a plurality of metal elements, such as films comprising a binary combination of metal elements. Aluminum and zirconium are examples of metals that can be deposited using ALD. Other metals that can be deposited include Mg, Si, Ca, Ti, V, Cr, Mn, Fe, Co, Ni, Cu, Zn, Ga, Ge, As, Se, Sr, Y, Nb, Mo, Ru, Rh, Pd, Ag, Cd, In, Sn, Sb, Ba, La, Hf, Ta, W, Re, Os, Ir, and Pt. Moreover, although much of the present disclosure focuses on the use of ALD to form metal films, oxide films, such as metal oxide films, can also be formed in the pores of the MOFs via ALD using, for example, repetitive metal-containing precursor/water exposure cycles.

The metallated MOFs can be used as catalysts for chemical reactions and in remediation applications. For example, some embodiments of the metallated MOFs comprise Lewis acidic sites that catalyze condensation reactions, as illustrated in the example below. Some embodiments of the metallated MOFs comprise sorption sites onto which species (e.g., metal elements, molecules or ions) from a sample (e.g., a vapor phase or liquid phase sample) are adsorbed or absorbed. For example, the metallated MOFs may be used for the capture of heavy toxic metals in water remediation application, or to remove harmful chemical and/or biological agents from the environment.

EXAMPLE

The example illustrates the synthesis and characterization of a Zr-based MOF (NU-1000), as well as the use of NU-1000 as a platform for quantitative, self-limiting metallation by AIM.

Materials

All compounds and solvents: 1,3,6,8-Tetrabromopyrene (Aldrich, 97%), (4-(methoxycarbonyl)phenyl)boronic acid (Combi-Blocks, 98%), $K_3PO_4$ (Aldrich), tetrakis(triphenylphosphine) palladium(0) (Strem Chemicals, 99%), benzoic acid (Aldrich, 99.5%), $ZrCl_4$ (Aldrich, 99.5%), hydrochloric acid (Aldrich, 37%), neat diethylzinc ($ZnEt_2$) (Aldrich, Zn 52 wt % minimum) and 1.1 M solution in toluene (Aldrich), neat trimethylaluminum ($AlMe_3$) (Aldrich, 36.3% Al) and 2.0 M solution in toluene (Aldrich), acetone (Macron, 98%), chloroform (BDH, 99.8%), 1,4-dioxane (Aldrich, 99.8%, anhydrous), N,N-dimethylformamide (DMF) (Macron, 99.8%), tetrahydrofuran (THF) (Macron, 99.0%), deuterated chloroform (d-$CDCl_3$) (Cambridge, 99.8%), deuterated dimethylsulfoxide ($d_6$-DMSO) (Cambridge, 99%), deuterated sulfuric acid ($D_2SO_4$) (Cambridge, 96-98% solution in $D_2O$) were used as received without further purification. n-pentane was dried on solvent still station before use.

Instrumentation.

$^1H$ NMR spectra were recorded on a 500 MHz Varian NOVA spectrometer and referenced to the residual solvent peak. Single crystals of NU-1000 were mounted in inert oil and transferred to the cold gas stream of a Bruker Kappa APEX CCD area detector equipped with a CuKα microsource with MX optics. Powder X-ray diffraction measurements were carried out on a Bruker MX IμS microsource with Cu Kα radiation and an Apex II CCD detector. The samples were mounted in capillaries as powders, sealed with wax and placed on a goniometer head. The data were collected on an area detector with rotation frames over 180° in $\phi$ and at $2\theta$ values of 12, 24, and 36° being exposed for 10 min at each frame. Overlapping sections of data were matched, and the resulting pattern was integrated using Broker's APEX2 phase ID program. The powder patterns were treated for amorphous background scatter. Optical images of NU-1000, crystals synthesized out of DEF, were obtained using a Nikon SMZ1500 stereozoom microscope coupled to a digital camera and PC (video monitor). Thermogravimetric analysis (TGA) was performed on a Mettler Toledo TGA under $N_2$ flow and heated from room temperature to 700° C. (at 10° C./min). Metallation reactions by ALD were carried out in a Savanah 5100 system (Ultratech Cambridge Nanotech) under $N_2$. Inductively coupled plasma-optical emission spectroscopy (ICP-OES) data were collected on Varian Vista MPX instrument. Diffuse reflectance infrared spectra (DRIFTS) were recorded on a Nicolet 7600 FTIR spectrometer equipped with an MCT detector. The spectra were either collected under Ar atmosphere (samples loaded in a drybox under Ar) or in a KBr mixture under $N_2$ purge (samples prepared in atmosphere). In both instances KBr was utilized as the background. $N_2$ adsorption isotherms were collected on either a Tristar II 3020 (Micromeritics) or ASAP 2020 (Micromeritics). All pore size distributions were obtained using a carbon slit pore model with a $N_2$ kernel (Micromeritics). Scanning electron microscopy images and energy dispersive spectroscopy profiles were collected on a Hitachi 5-4800-II.

Synthesis of 1,3,6,8-tetrakis(p-benzoic acid)pyrene 1,3,6,8-tetrakis(p-benzoic acid)pyrene (TBAPy)

Scheme 1. Synthetic scheme and yields for $H_4$TBAPy.

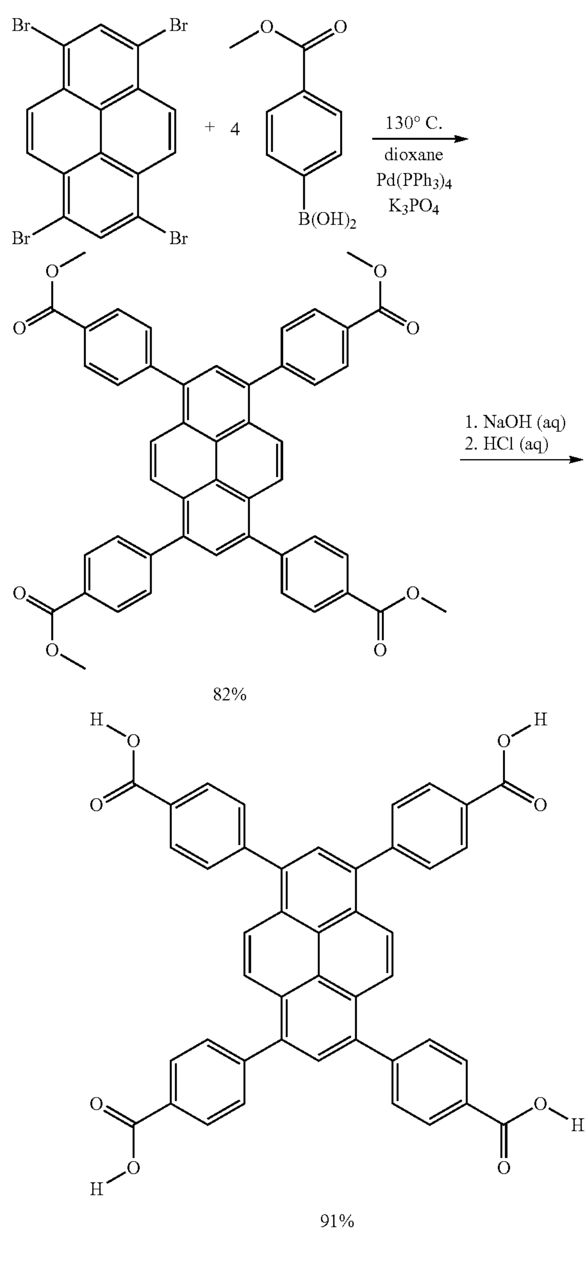

1,3,6,8-tetrakis(4-(methoxycarbonyl)phenyl)pyrene

A mixture of (4-(methoxycarbonyl)phenyl)boronic acid (1.040 g, 5.80 mmol), 1,3,6,8-tetrabromopyrene (0.500 g, 0.97 mmol), tetrakis(triphenylphosphine) palladium(0) (0.030 g 0.026 mmol), and potassium tribasic phosphate (1.100 g, 5.30 mmol) in dry dioxane (20 mL) was loaded (in a glovebox) into a 20 mL microwave vial (Biotage) and capped. This mixture was stirred under argon for 72 h at 130° C. in an oil bath. The reaction mixture was evaporated to dryness and the solid residue was washed with water to remove inorganic salts. The insoluble material was extracted with chloroform (three times by 50 mL), the extract was dried over magnesium sulfate, and the solvent volume was reduced under vacuum. The residue was boiled in tetrahydrofuran for 2 h and filtered; the resulting filtrate contained mainly impurities. This procedure gave 0.58 g of 1,3,6,8-tetrakis(4-(methoxycarbonyl)phenyl)pyrene (82% yield).

$^1$H NMR ($CDCl_3$-d): δ 3.99 (s, 12H), 7.75 (d, 8H), 8.01 (s, 2H), 8.15 (s, 4H), 8.23 (d, 8H).

1,3,6,8-tetrakis(p-benzoic acid)pyrene

To a 250 mL round bottom flask containing 0.58 g (0.78 mmol) of solid 1,3,6,8-tetrakis(4-(methoxycarbonyl)phenyl) pyrene, a solution containing 1.5 g (37.5 mmol) NaOH in 100 mL of a THF/water (ratio 1:1) mixture was added and the resultant suspension was vigorously stirred under reflux overnight. The solvents were removed under vacuum and water was added to the residue which formed a clear yellow solution. The clear yellow solution was stirred at room temperature for 2 h and the pH value was adjusted to 1 using concentrated HCl. The resulting yellow solid was collected by filtration, and washed with water several times. The crude product was recrystallized from DMF, filtered, washed with chloroform and dried under vacuum. This gave 0.49 g (91%) of the pure product $H_4$TBAPy.

$^1$H NMR (DMSO-$d_6$): δ 7.86 (d, 8H), 8.09 (s, 2H), 8.17 (d, 8H), 8.21 (s, 4H), 13.12 (s, 4H).

Synthesis of $Zr_6(\mu_3\text{-}OH)_8(OH)_8(TBAPy)_2$ (NU-1000).

Synthesis of NU-1000 in DEF 70 mg of $ZrCl_4$ (0.30 mmol) and 2700 mg (22 mmol) of benzoic acid were mixed in 8 mL of DEF (in a 6-dram vial) and ultrasonically dissolved. The clear solution was incubated in an oven at 80° C. for 1 h. After cooling down to room temperature 40 mg (0.06 mmol) of $H_4$TBAPy was added to this solution and the mixture was sonicated for 20 min. The yellow suspension was heated in an oven at 120° C. for 48 h. After cooling down to room temperature, yellow single crystals were present on the vial walls. The sample was washed with DMF and subsequently activated with HCl, as described below.

Synthesis of NU-1000 in DMF 70 mg of $ZrCl_4$ (0.30 mmol) and 2700 mg (22 mmol) of benzoic acid were mixed in 8 mL of DMF (in a 6-dram vial) and ultrasonically dissolved. The clear solution was incubated in an oven at 80° C. for 1 h. After cooling down to room temperature 40 mg (0.06 mmol) of $H_4$TBAPy was added to this solution and the mixture was sonicated for 20 min. The yellow suspension was heated in an oven at 120° C. for 48 h. After cooling down to room temperature, yellow polycrystalline material was isolated by filtration (35 mg of activated material, 54% yield) and washed with DMF and subsequently activated with HCl, as described below.

Elemental analysis data for molecular formula $Zr_6(OH)_8(TBAPy)_2(\text{benzoic acid})_4$: C, H, N, Cl Theoretical: 55.6%, 2.1%, 0%, 0%; Experimental: 53.8%, 3.1%, 0.1%, 0.4%. Elemental analysis data for molecular formula {0.75*[$Zr_6$ $(OH)_8(TBAPy)_2$(benzoic acid)$_4$]+0.25*[$Zr_6(O)_4(OH)_4]_2(TBAPy)_6$]}: C, H, N, Cl Theoretical: 56.4%, 2.2%, 0%, 0%; Experimental: 53.8%, 3.1%, 0.1%, 0.4%.

Activation Procedure for NU-1000.

As synthesized NU-1000 was activated using a slightly modified method previously reported by Feng et al. (See, Feng, D.; Gu, Z.-Y.; Li, J.-R.; Jiang, H.-L.; Wei, Z.; Zhou, H.-C. *Angew. Chem. Int. Ed.* 2012, 51, 10307.) Approximately 40 mg of solvated ("wet") material was soaked in 12 ml of DMF and 0.5 ml of 8 M aqueous HCl was added. This mixture was heated in an oven at 100° C. for 24 h. After cooling to room temperature, the solution was removed and the material was washed twice with DMF to remove HCl impurities. Subsequently the solid residue was washed twice with acetone and soaked in acetone for additional 12 h. NU-1000 was filtered, briefly dried on a filter paper and activated at 120° C. under vacuum for 12 h on the preparation station of ASAP 2020 instrument. Shown below, the as synthesized NU-1000 sample was characterized by $^1H$ NMR, $N_2$ adsorption measurements, and DRIFTS. The data are consistent with the removal of benzoic acid from the $Zr_6$ node and the incorporation of —OH groups.

Elemental analysis data for molecular formula $Zr_6(OH)_8(TBAPy)_2$: C, H, N, Cl Theoretical: 48.7%, 2.4%, 0%, 0%; Experimental: 49.1%, 3.0%, 0.3%, 0.4%. Elemental analysis data for molecular formula {0.75*[$Zr_6(OH)_8(TBAPy)_2$]+0.25*[$Zr_6(O)_4(OH)_4]_2(TBAPy)_6$]}: C, H, N, Cl Theoretical: 51.6%, 2.5%, 0%, 0%; Experimental: 49.1%, 3%, 0.3%, 0.4%.

Synthesis of Zn-AIM and Al-AIM by ALD

Approximately 20-30 mg of NU-1000 was loaded into a home built stainless steel powder holder and subsequently placed into a ALD reactor. NU-1000 was allowed to equilibrate in the reactor for 0.5 h prior to the ALD deposition. The ALD reactions were carried out utilizing the following timing sequence (time in s): $t_1$-$t_2$-$t_3$, where $t_1$ is the precursor pulse time, $t_2$ the precursor exposure time (i.e., the time where the precursor is in contact with NU-1000 without pumping), and $t_3$ the $N_2$ purge time. $ZnEt_2$ was deposited at 140° C. utilizing five 1-120-120 sequences and $AlMe_3$ was deposited at 120° C. utilizing twenty 0.015-1-1 sequences. During $t_1$ and $t_2$ the $N_2$ flow rate was 5 sccm, while during $t_3$ the $N_2$ flow rate was 20 sccm.

Synthesis of Zn-NU-1000 and Al-NU-1000 from Solution

Zn-NU-1000.

In a glovebox, 30 mg (0.014 mmol) of activated NU-1000 was loaded into a 5 mL microwave vial (Biotage) and 4.0 mL of 1.1 M (4.4 mmol, ca. 20-fold excess per —OH group in NU-1000) $ZnEt_2$ in toluene was added. The vial was capped and left for 24 h at room temperature. The solution was removed and the remaining yellow solid was washed once with n-pentane and left soaked in 5 mL of pentane for additional 24 h to wash out unreacted $ZnEt_2$. Briefly dried Zn-NU-1000 was transferred in a glovebox to a Tristar sample tube and activated under vacuum on ASAP 2020 at 120° C. for 12 h. Approximately 2 mg of activated Zn-NU-1000 was exposed to air and digested in $d_6$-DMSO/$D_2SO_4$ mixture for $^1H$ NMR analysis.

Al-NU-1000.

In a glovebox, 30 mg (0.014 mmol) of activated NU-1000 was loaded into a 5 mL microwave vial (Biotage) and 2.2 mL of 2 M (4.4 mmol) $AlMe_3$ in toluene was added dropwise. During addition of the organometallic compound intense gas evolution was observed and after few minutes initially yellow powder of NU-1000 turned orange. The vial was capped and left for 24 h at room temperature. The solution was removed and the remaining solid was washed once with n-pentane and left soaked in 5 mL of pentane for additional 24 h to wash out unreacted $AlMe_3$. Briefly dried Al-NU-1000 was transferred in a glovebox to a Tristar sample tube and activated under vacuum on ASAP 2020 at 120° C. for 12 h. Approximately 2 mg of activated Al-NU-1000 was exposed to air and digested in $d_6$-DMSO/$D_2SO_4$ mixture for $^1H$ NMR analysis.

Single Crystal X-Ray Structure of NU-1000 (from DEF).

Single crystals of $C_{88}H_{44}O_{32}Zr_6$ (NU-1000) were obtained from DEF, mounted in inert oil, and transferred to the cold gas stream of a Bruker Kappa APEX CCD area detector equipped with a CuKα microsource with MX optics.

NU-1000 Residual Electron Density Plots

Figure 7:
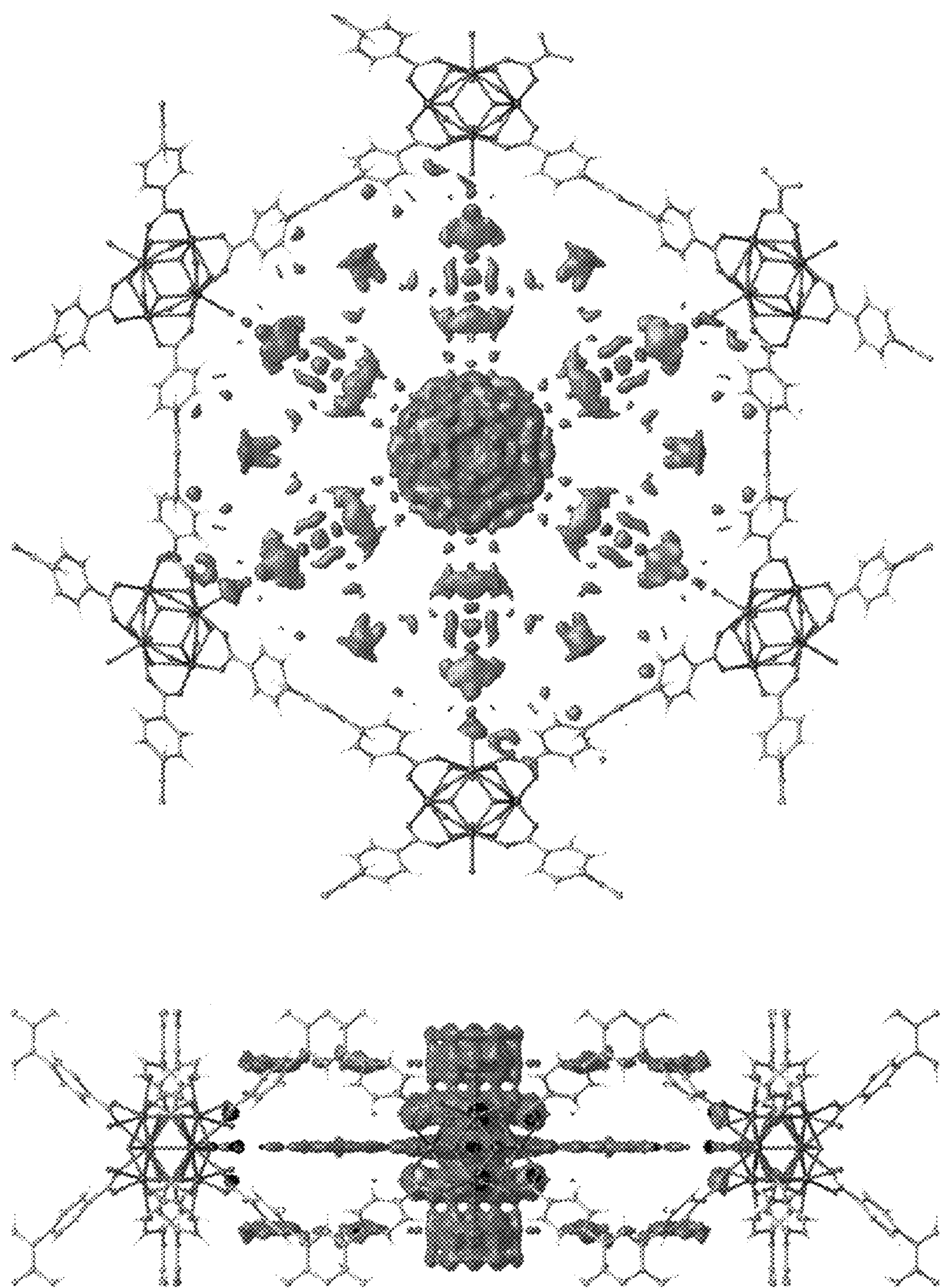
FIG. 7. Residual electron density plots of the secondary framework observed within the mesopores of NU-1000.

During the structure refinement of NU-1000 the presence of a partially occupied, and disordered, framework within the mesopores of NU-1000 was observed. The residual electron density showed evidence of a disordered node and ligands. The essence of this secondary framework was captured in residual electron density plots (FIG. 7), which based on the Q peaks was estimated to be present in ~20% of the mesopores of NU-1000.

ICP-OES Analysis.

Approximately 2 mg of sample (e.g., Zn-AIM) was weighed out on a TGA balance. The powder was transferred to a microwave vial (4 mL) and 0.25 mL concentrated $H_2O_2$ and 0.75 mL concentrated $H_2SO_4$ were added. The vial was capped and irradiated in a microwave oven at 150° C. for 5 min. The resultant clear solution was diluted to 25 mL with nanopure water and analyzed via ICP-OES. Zn and Al concentrations were calculated from external stock solutions and compared to the known Zr content of the MOF.

Volumetric Isotherms for NU-1000, Zn-AIM, and Al-AIM.

Volumetric isotherms were calculated by using the metal loading, determined by ICP-OES, in Table 1. It was assumed that —$Zn(C_2H_5)$ and —$Al(CH_3)_2$ were bound to the —OH groups of the $Zr_6$ nodes (i.e., the following stoichiometry was assumed $Zn(C_2H_5)_2$+Zr—OH→ZrO—$Zn(C_2H_5)$ and $Al(CH_3)_3$+Zr—OH ZrO—$Al(CH_3)_2$). The crystallographically predicted densities of 0.49 cc/g for NU-1000, 0.55 cc/g for Zn-AIM, and 0.59 cc/g for Al-AIM were used.

Results.

Solvothermal reactions of $ZrCl_4$, 1,3,6,8-tetrakis(p-benzoic acid)pyrene ($H_4TBAPy$), and benzoic acid in diethylformamide (DEF) yielded crystals suitable for single-crystal X-ray analysis. (See, Stylianou, K. C.; Heck, R.; Chong, S. Y.; Bacsa, J.; Jones, J. T. A.; Khimyak, Y. Z.; Bradshaw, D.; Rosseinsky, M. J. *J. Am. Chem. Soc.* 2010, 132, 4119; Stylianou, K. C.; Rabone, J.; Chong, S. Y.; Heck, R.; Armstrong, J.; Wiper, P. V.; Jeffs, K. E.; Zlatogorsky, S.; Bacsa, J.; McLennan, A. G.; Ireland, C. P.; Khimyak, Y. Z.; Thomas, K. M.; Bradshaw, D.; Rosseinsky, M. J. *J. Am. Chem. Soc.* 2012, 134, 20466.) The parent-framework node was composed of an octahedral $Zr_6$ cluster capped by eight $\mu_3$-OH ligands. Eight of the twelve octahedral edges are connected to TBAPy units, while the remaining Zr coordination sites (after activation) are occupied by eight terminal —OH ligands. The 3-D structure can be described as 2-D Kagome sheets linked by TBAPy ligands. Four of the eight terminal —OH groups point into the mesoporous channels, while the remaining terminal hydroxyls lie in smaller apertures between the Kagome sheets. The resultant MOF (FIG. 2) has the molecular formula $Zr_6(\mu_3\text{-}OH)_8(OH)_8(TBAPy)_2$, which we have designated NU-1000. We observe that ~20-25% of the mesoporous channels contain a secondary structural element based on residual electron density plots and $N_2$ adsorption simulations. We modeled the secondary element as $[Zr_6(\mu_3\text{-}O)_4(\mu_3\text{-}OH)_4]_2(TBAPy)_6$ which connects to twelve $Zr_6$ nodes of the parent framework through six TBAPy ligands. Finally NU-1000 was activated with a HCl/N,N-dimethylformamide (DMF) mixture similar to the procedure of Feng et al. (See, Feng, D.; Gu, Z.-Y.; Li, J.-R.; Jiang, H.-L.; Wei, Z.; Zhou, H.-C. *Angew. Chem. Int. Ed.* 2012, 51, 10307.) $^1$H NMR and diffuse reflectance infrared Fourier transform spectroscopy (DRIFTS) reveal that HCl removes benzoic acid from the $Zr_6$ nodes, leaving behind terminal —OH groups.

We initiated AIM (vide infra) with a microcrystalline powder of NU-1000, reasoning that this form would facilitate diffusion of ALD precursors within the MOF. The microcrystalline powder was obtained by switching to DMF as a synthesis solvent. The powder X-ray diffraction (PXRD) patterns of the DEF (simulated) and DMF prepared samples are identical and Pawley refinement of the DMF pattern demonstrates that the unit cell and symmetry are identical as well. The remainder of this example will discuss DMF prepared samples only.

Figure 4:
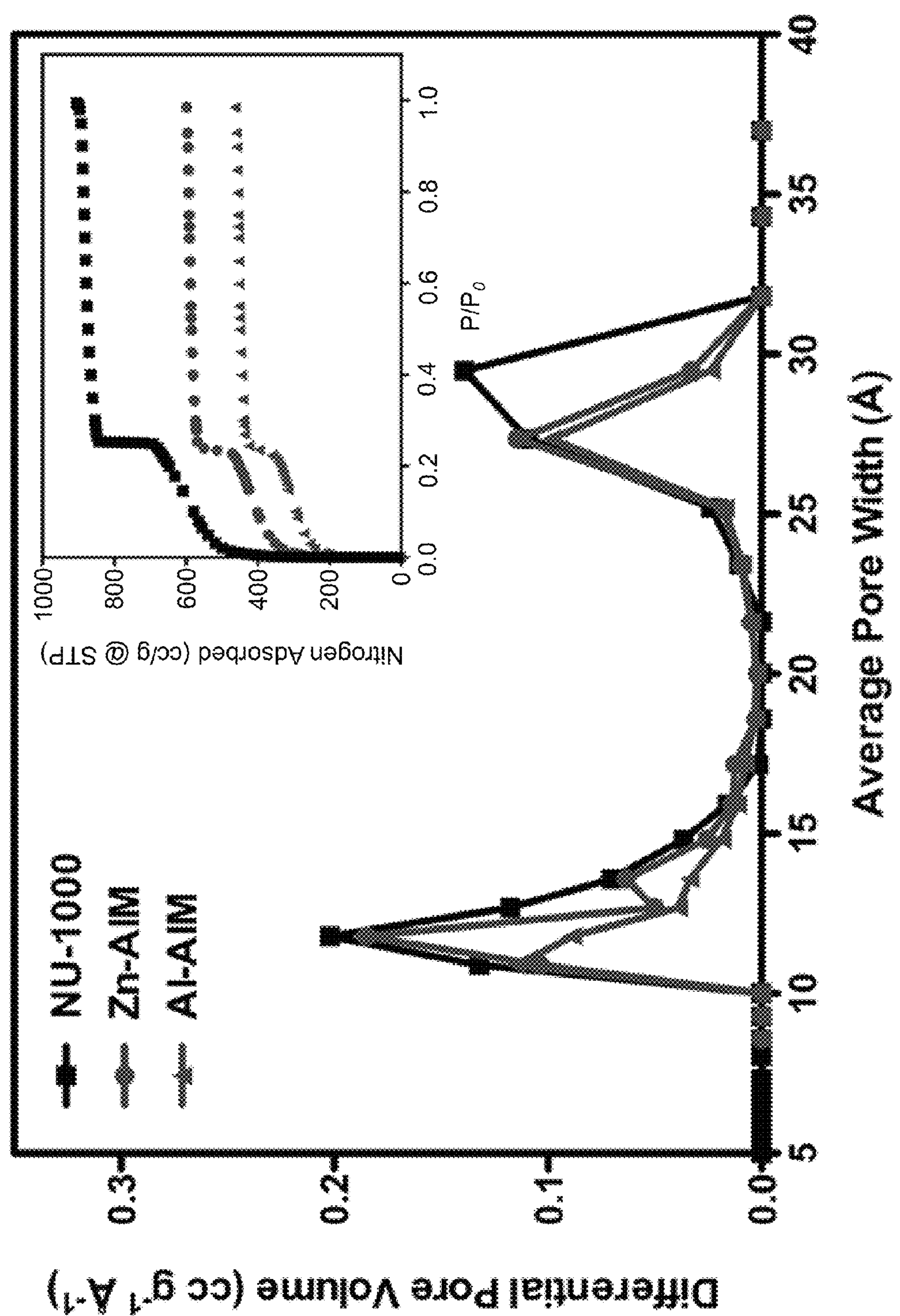
FIG. 4. DFT pore size distributions and $N_2$ adsorption isotherms (inset) for NU-1000, Zn-AIM, and Al-AIM.

The $N_2$ adsorption isotherm of NU-1000 is best described as type IVc (FIG. 4); NU-1000 has a Brunauer-Emmett-Teller (BET) surface area of 2320 $m^2\ g^{-1}$ and a total pore volume of 1.4 $cm^3\ g^{-1}$. The experimentally measured surface area and total pore volumes are in excellent agreement with the theoretical values of 2280 $m^2\ g^{-1}$ and 1.4 $cm^3\ g^{-1}$ obtained from grand canonical Monte Carlo simulations (GCMC) and subsequent BET analysis. DFT analyzed pore-size distributions indicate pores of diameter at ~12 Å and 30 Å, consistent, respectively, with the triangular micropores and hexagonal mesopores of NU-1000. Thermal gravimetric analysis (TGA) of a sample activated at 120° C. demonstrated that NU-1000 is stable up to 500° C. The presence of —OH groups was confirmed by DRIFTS. Sharp peaks appear at wavenumbers 3674 and 3655 $cm^{-1}$ (black curve in FIG. 4), which we have assigned to the terminal and bridging —OH stretches of the $Zr_6(\mu_3\text{-}OH)_8(OH)_8$ node. TGA and temperature-dependent-DRIFTS data are also quantitatively consistent with the assigned —OH content of NU-1000. In addition, the temperature-dependent DRIFTS data demonstrate that the —OH functionality persists under the conditions of our ALD experiments (vide infra).

Microcrystalline samples of NU-1000 were placed in an ALD reactor at 140° C. or 110° C. and exposed to diethylzinc ($ZnEt_2$) or $AlMe_3$. The ALD reactions were carried out with the following timing sequence (in seconds): $t_1$-$t_2$-$t_3$, where $t_1$ is the precursor pulse time, $t_2$ the precursor exposure time, and $t_3$ the $N_2$ purge time. Metallation was confirmed via inductively coupled plasma-optical emission spectroscopy (ICP-OES). The resultant materials have been termed Zn-AIM and Al-AIM for Zn- and Al-Atomic layer deposition In a MOF. On average we observe 0.5 Zn or 1.4 Al atoms per Zr atom, Table 1. These values correspond to three Zn, or eight Al, atoms for every $Zr_6$ node in NU-1000. Consistent with ALD-like behavior, longer exposure times, via repeated precursor exposure, did not lead to greater metal loading. To ascertain whether we were fully accessing NU-1000 under our ALD conditions, we extended exposure times to several hours, rather than seconds, by immersing samples in solutions containing $ZnEt_2$ or $AlMe_3$ (Table 1, Zn-NU-1000 and Al-NU-1000). The loadings obtained through extended solution-phase exposure are only slightly higher than those from transient ALD.

TABLE 1

ICP-OES, BET Surface Areas, and Pore Volumes for NU-1000, Zn-AIM, Al-AIM, Zn-NU-1000, and Al-NU-1000.

| MOF | Metal: Zr | Metal: $Zr_6$ | BET Surface Area ($m^2\ g^{-1}$) | Pore Volume ($cm^3\ g^{-1}$) |
|---|---|---|---|---|
| NU-1000 | — | — | 2320 | 1.4 |
| Zn-AIM [a] | 0.5 | 3.0 | 1580 | 0.9 |
| Al-AIM [b] | 1.4 | 8.1 | 1160 | 0.7 |
| Zn-NU-1000 | 0.6 | 3.6 | 1710 | 1.0 |
| Al-NU-1000 | 1.7 | 10.0 | 1290 | 0.7 |

[a] $t_1$ = 1 s, $t_2$ = 120 s, $t_3$ = 120 s

[b] $t_1$ = 0.015 s, $t_2$ = 1 s, $t_3$ = 1 s.

Figure 3:
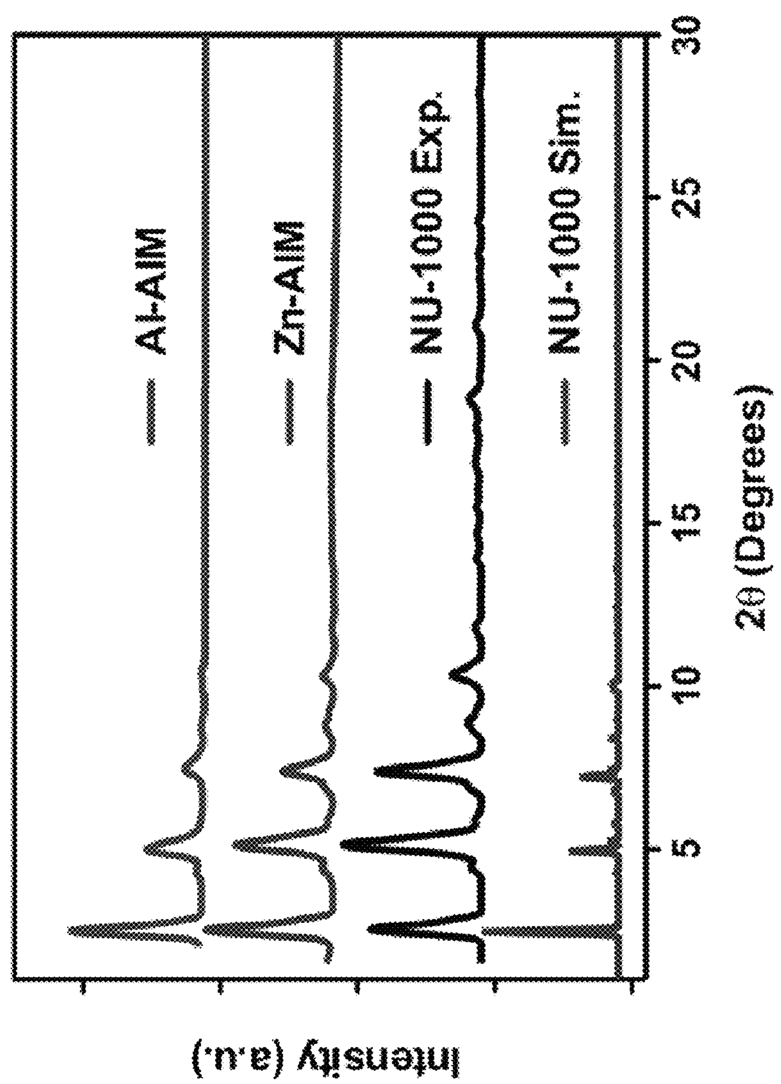
FIG. 3. PXRD Patterns of NU-1000 simulated (Sim.), NU-1000 experimental (Exp.), Zn-AIM, and Al-AIM.

PXRD measurements (FIG. 3) showed that both Zn-AIM and Al-AIM retain their crystallinity. BET analyses of the $N_2$ adsorption isotherms (FIG. 4) indicate a decrease in surface area from 2230 $m^2/g$ for NU-1000, to 1580 and 1160 $m^2/g$ for Zn-AIM and Al-AIM. The gravimetric and volumetric surface areas, along with total pore volumes, decrease with increasing metal loading (Table 1). DFT pore-size distributions (FIG. 4), extracted from the $N_2$ isotherms, indicate that the average diameter of the mesopore shifts from ~30 Å in NU-1000 to ~27 Å for both Zn-AIM and Al-AIM.

Figure 5:
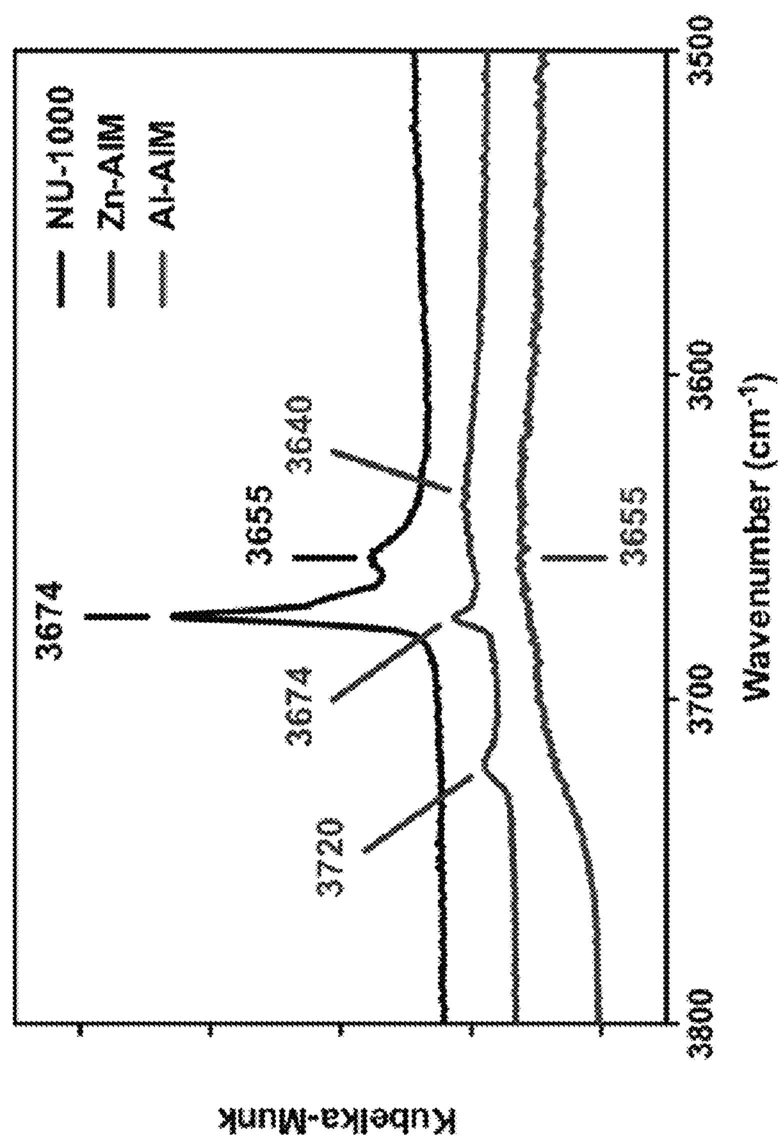
FIG. 5. DRIFTS spectra for NU-1000, Zn-AIM and Al-AIM.
Figure 6:
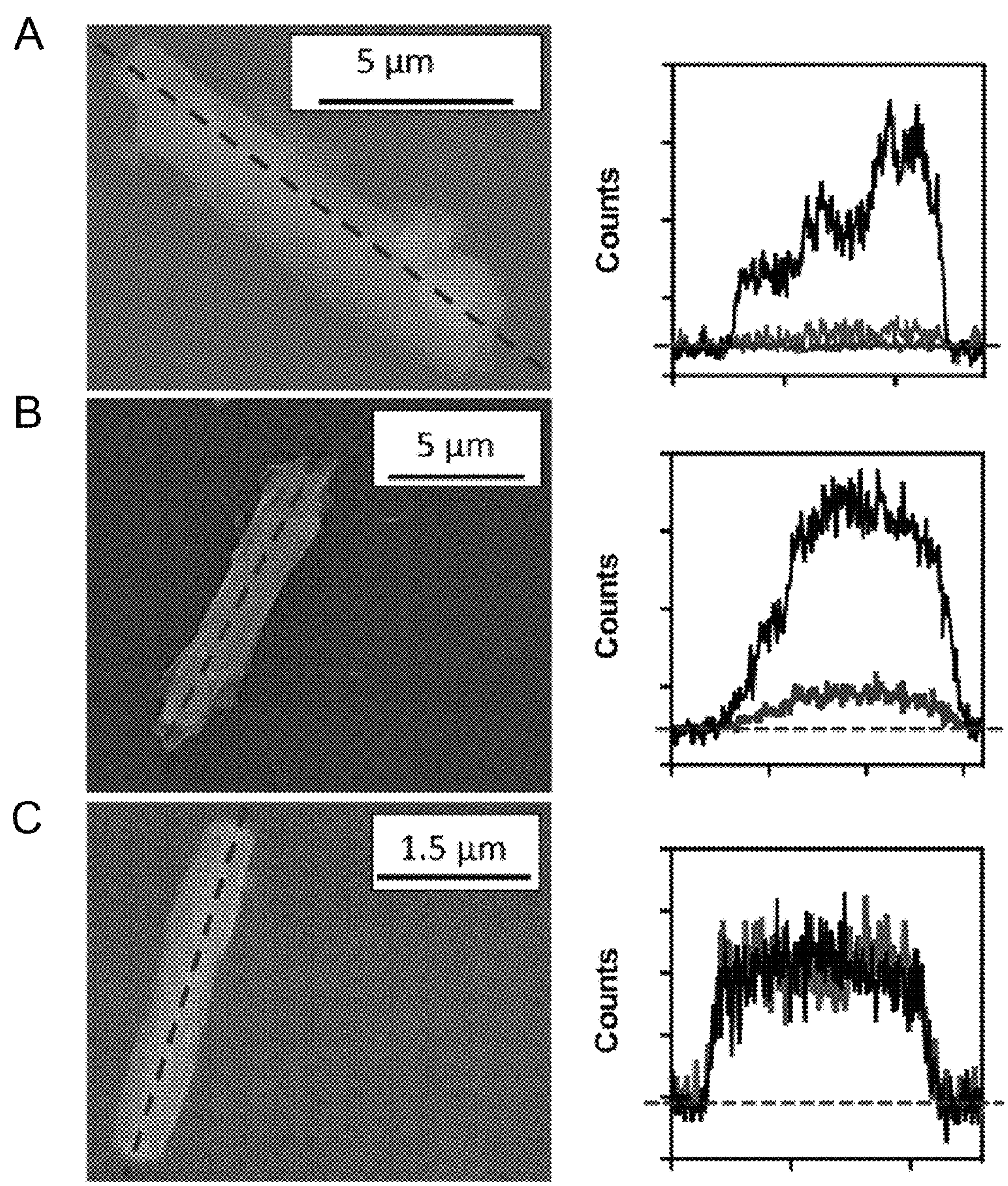
FIG. 6. SEM-EDX images and spectra of NU-1000 (A), Zn-AIM (B), and Al-AIM (C). The dashed line indicates where the EDX scan was taken.

DRIFTS measurements (FIG. 5) confirmed that metallation occurs by reaction with —OH groups. Clearly the sharp peaks at 3674 $cm^{-1}$ and 3655 $cm^{-1}$ have been significantly or completely reduced. The DRIFTS data suggest that $ZnEt_2$ is able to react with —OH groups pointing into the large hexagonal channels, while $AlMe_3$ reacts with all terminal —OH groups. To assess Zn and Al incorporation by individual MOF microcrystallites, we turned to scanning electron microscopy-energy dispersive X-ray spectroscopy (SEM-EDX). As shown in FIG. 6A, only Zr (upper trace) was detected in NU-1000; Zn (lowest trace) and Al (middle trace) do not rise above the baseline. The blue line indicates where, spatially in the image, the EDX scan was performed over. When scanning Zn- and Al-AIM (FIGS. 6B and 6C), Zn (lower trace) and Al (lighter trace) were detected throughout the entire NU-1000 crystal.

To demonstrate that AIM could be utilized to elicit new functional behavior we turned to chemical catalysis. The Knoevenagel condensation between ethyl cyanoacetate and benzaldehyde can be catalyzed by Lewis acids, albeit in limited scope and conversion rate. (See, Cui, H.-F.; Dong, K.-Y.; Zhang, G.-W.; Wang, L.; Ma, J.-A. *Chem. Commun.* 2007, 2284.) The $Zr^{IV}$ sites in NU-1000 proved inactive towards the Knoevenagel condensation. In contrast, Zn-AIM and Al-AIM were active catalysts, which we attribute to the presence of Lewis acidic $Al^{III}$ and $Zn^{II}$ sites in Zn- and Al-AIM. While AIM, as implemented here, leaves methyl or ethyl ligand(s) on the incorporated metal ions, these are highly reactive and will be removed and released as methane or ethane shortly after exposure to benzaldehyde. After catalysis, the solutions were filtered to remove the MOF and examined by ICP-OES; consistent with the assignment of Zn- and Al-AIM as the catalysts, no Zn or Al was found in solution. The results demonstrate the potential for ALD to incorporate spatially oriented single-site-like catalytic moieties into ultrahigh-aspect-ratio MOFs.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method of metallating a porous metal-organic framework comprising inorganic nodes and organic linkers, the method comprising depositing a film comprising a metal on the surfaces within the pores of the metal-organic framework via atomic layer deposition.

2. The method of claim 1, wherein the inorganic nodes of the metal-organic framework comprise zirconium.

3. The method of claim 1, wherein the film comprises zinc or aluminum.

4. The method of claim 1, wherein the film comprises only a single metal element.

5. The method of claim 1, wherein the film comprises a binary combination of metals.

6. The method of claim 1, wherein the film comprises a metal oxide.

7. The method claim 1, wherein the metal-organic framework comprises channels having an average pore size in the range from about 2 to about 50 nm.

8. The method of claim 1, wherein the surfaces within the pores of the porous metal-organic framework are functionalized with hydroxyl groups.

9. The method of claim 2, wherein the metal-organic framework comprises channels having an average pore size in the range from about 2 to about 50 nm.

10. A method of metallating a porous metal-organic framework comprising inorganic nodes and organic linkers, the method comprising depositing a film comprising a metal on the surfaces within the pores of the metal-organic framework via atomic layer deposition, wherein the inorganic nodes comprise an octahedral $Zr_6$ cluster capped by eight $\mu_3$-ligands and have eight octahedral edges, the linkers comprise 1,3,6,8-tetrakis(p-benzoic acid)pyrene units, and eight of the octahedral edges are connected to the 1,3,6,8-tetrakis(p-benzoic acid)pyrene units and further wherein the $\mu_3$-ligands are hydroxo ligands, oxo ligands or aquo ligands.

11. The method of claim 10, wherein the $\mu_3$-ligands comprise hydroxo ligands.

12. The method of claim 1, wherein the metal comprises Lewis acidic sites that are capable of catalyzing condensation reactions.

13. The method of claim 2, wherein the inorganic nodes are hexa-$Zr^{IV}$ nodes and the organic linkers are tetratopic linkers.

14. The method of claim 1, wherein the film consists of metal.

* * * * *